United States Patent
Sjolin

(10) Patent No.: US 10,247,833 B2
(45) Date of Patent: Apr. 2, 2019

(54) MEASUREMENT CIRCUIT FOR AN X-RAY DETECTOR, AND A CORRESPONDING METHOD AND X-RAY IMAGING SYSTEM

(71) Applicant: Prismatic Sensors AB, Stockholm (SE)

(72) Inventor: Martin Sjolin, Stockholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 15/505,374

(22) PCT Filed: May 3, 2016

(86) PCT No.: PCT/SE2016/050389
§ 371 (c)(1),
(2) Date: Feb. 21, 2017

(87) PCT Pub. No.: WO2017/123128
PCT Pub. Date: Jul. 20, 2017

(65) Prior Publication Data
US 2018/0217277 A1    Aug. 2, 2018

Related U.S. Application Data

(60) Provisional application No. 62/278,736, filed on Jan. 14, 2016.

(51) Int. Cl.
| | |
|---|---|
| *G01T 1/24* | (2006.01) |
| *G06T 11/00* | (2006.01) |
| *A61B 6/03* | (2006.01) |
| *A61B 6/00* | (2006.01) |

(52) U.S. Cl.
CPC ............... *G01T 1/24* (2013.01); *A61B 6/032* (2013.01); *A61B 6/4266* (2013.01); *A61B 6/5205* (2013.01); *G06T 11/00* (2013.01)

(58) Field of Classification Search
CPC ..... A61B 6/032; A61B 6/4266; A61B 6/5205; G01T 1/24; G06T 11/00
See application file for complete search history.

(56) References Cited

U.S. PATENT DOCUMENTS

2010/0278451 A1* 11/2010 Spahn ..................... G06T 3/40
                                                                 382/294
2015/0230772 A1    8/2015 Yamazaki
2015/0324973 A1    11/2015 Ueki et al.

FOREIGN PATENT DOCUMENTS

EP      2 664 280 A2    11/2013

OTHER PUBLICATIONS

International Search Report, dated Nov. 28, 2016, from corresponding PCT application.

* cited by examiner

*Primary Examiner* — Mark R Gaworecki
(74) *Attorney, Agent, or Firm* — Young & Thompson

(57) ABSTRACT

There is provided a measurement circuit (30) for an x-ray detector (5). The measurement circuit (30) is configured to sample measurement data to generate data points and process the data points before read-out to produce new data points by combining two or more data points which have been acquired at different times such that the number of data points for read-out are less than the number of original data points.

18 Claims, 8 Drawing Sheets

MEASUREMENT CIRCUIT FOR AN X-RAY DETECTOR, AND A CORRESPONDING METHOD AND X-RAY IMAGING SYSTEM

TECHNICAL FIELD

The proposed technology relates to a measurement circuit for an x-ray detector, a method for processing data by a measurement circuit of an x-ray detector prior to data read-out and an x-ray imaging system comprising a measurement circuit.

BACKGROUND

Radiographic imaging such as x-ray imaging has been used for years in medical applications and for non-destructive testing.

Normally, an x-ray imaging system includes an x-ray source and an x-ray detector array consisting of multiple detectors comprising one or many detector elements (independent means of measuring x-ray intensity/fluence). The x-ray source emits x-rays, which pass through a subject or object to be imaged and are then registered by the detector array. Since some materials absorb a larger fraction of the x-rays than others, an image is formed of the subject or object.

An example of a commonly used x-ray imaging system is an x-ray Computed Tomography (CT) system, which may include an x-ray tube that produces a fan- or cone beam of x-rays and an opposing array of x-ray detectors measuring the fraction of x-rays that are transmitted through a patient or object. The x-ray tube and detector array are mounted in a gantry that rotates around the imaged object. An example illustration of a CT geometry is shown in FIG. 1.

The dimensions and segmentation of the detector array affect the imaging capabilities of the CT apparatus. A plurality of detector elements in the direction of the rotational axis of the gantry, i.e. the z-direction of FIG. 1 enables multi-slice image acquisition. A plurality of detector elements in the angular direction ($\xi$ in FIG. 1) enables measurement of multiple projections in the same plane simultaneously and this is applied in fan/cone-beam CT. Most conventional detectors are so called flat-panel detectors, meaning that they have detector elements in the slice (z) and angular ($\xi$) directions.

X-ray detectors made from low-Z materials need to have a substantial thickness in the direction of the x-ray beam in order to have sufficient detection efficiency to be used in CT. This can be solved by, for example, using an "edge-on" geometry, as in U.S. Pat. No. 8,183,535, in which the detector array is built up of a multitude of detectors, which comprise thin wafers of a low-atomic number material, oriented with the edge towards the impinging x-rays. An example illustration of a CT geometry using edge-on detectors is shown in FIG. 2, showing the position of the source 60, the direction of the x-rays 45, the detector array 50, a single edge-on detector 5 and the angular direction of movement of the array 55. It is common that each detector has a plurality of detector elements on a 2D grid on the wafer.

FIG. 3 is a schematic diagram illustrating a semiconductor detector module implemented as a multi-chip module similar to an exemplary embodiment in U.S. Pat. No. 8,183,535. In this example, the detector elements are organized in three depth segments 15 with respect to the direction of the incoming x-rays 45. This example shows how the semiconductor sensor also can have the function of substrate 5 in a Multi-Chip Module (MCM). The signal is routed 37 from the detector elements 15 to inputs of parallel processing circuits (e.g. ASICs) 30. It should be understood that the term Application Specific Integrated Circuit (ASIC) is to be interpreted broadly as any general circuit used and configured for a specific application. The ASIC processes the electric charge generated from each x-ray and converts it to digital data, which can be used to obtain measurement data such as a photon count and/or estimated energy. The ASICs are configured for connection to digital data processing circuitry 20 so the digital data may be sent to further digital data processing and/or memories located outside of the MCM and finally the data will be the input for image processing to generate a reconstructed image.

For a given rotational position, each detector element measures the transmitted x-rays for a certain projection line. Such a measurement is called a projection measurement. The collection of projection measurements for many projection lines is called a sinogram. The sinogram data is utilized through image reconstruction to obtain an image of the interior of the imaged object. Each projection line (a point in the sinogram) is given by an angular coordinate, $\theta$, and a radial coordinate, r, as defined in FIG. 4. Each measurement with a detector element at a specific coordinate given by (r, $\theta$) is a sample of the sinogram. More samples in the sinogram generally lead to a better representation of the real sinogram and therefore also a more accurately reconstructed image. An example of how a detector array, similar to that displayed in FIG. 1, samples the sinogram space is shown in FIGS. 6A-B for two different angular positions of the gantry separated by $\Delta\theta$. The different r positions of the samples come from the different detectors in the array.

Generally, the gantry rotates continuously and each detector element measures the x-rays flux within a frame time. A measurement period, T, is here defined as the interval in time during which a certain detector element is occupied with a measurement. The length of the measurement period can be, but does not have to be, equal to the frame time. The measurement period is much smaller than the total data acquisition time and multiple measurement periods follow directly after each other throughout the overall data acquisition/measurement. The length of the measurement period is referred to as the temporal sampling interval and the reciprocal of the sampling interval 1/T is referred to as the sampling frequency. The angular sampling interval of the CT system is given by the angular velocity of the gantry, $\omega = d\theta/dt$, and the temporal sampling interval, T, via $\Delta\theta = \omega T$. A schematic example illustration of the angular sampling is displayed in FIG. 5, where the detector and the source are illustrated for two different positions separated in time by the sampling interval T. The radial coordinate for all projection lines corresponding to a specific detector element is invariant to the rotation of the gantry.

In order to perform an accurate image reconstruction from tomographic data, it is essential that there is a sufficient amount of angular samples. Insufficient angular sampling can lead to artifacts in the image, aliasing and poor resolution.

One way to increase the angular sampling frequency is to decrease the temporal sampling interval T. Decreasing the temporal sampling interval results in a corresponding increase in the amount of produced data.

The temporal sampling rate can be limited by the capacity of the data transfer from the measurement circuit, rather than the measurement circuit itself.

SUMMARY

It is an object to enable accurate image reconstruction, even if there is a limited temporal sampling rate.

It is also an object to provide a measurement circuit for an x-ray detector.

Another object is to provide a method for processing data by a measurement circuit of an x-ray detector prior to data read-out.

Yet another object is to provide an x-ray imaging system comprising such a measurement circuit.

According to a first aspect there is provided a measurement circuit for an x-ray detector. The measurement circuit is configured to sample measurement data to generate data points and process the data points before read-out to produce new data points by combining two or more data points which have been acquired at different times such that the number of data points for read-out are less than the number of original data points.

According to a second aspect there is provided a method for processing data by a measurement circuit of an x-ray detector prior to data read-out, wherein new data points are produced by combining two or more data points which have been acquired by the measurement circuit at different times such that the number of data points which are read out are less than the number of original data points.

According to a third aspect, there is provided an x-ray imaging system comprising a measurement circuit according to the first aspect.

According to a fourth aspect, there is provided a measurement circuit for an x-ray detector having a number of detector elements. The measurement circuit is configured for connection to the detector elements of the x-ray detector to obtain measurement data. The measurement circuit is configured to sample the measurement data to generate data samples, also referred to as sampled data points. The measurement circuit is further configured to process the sampled data points before read-out to produce new data points for read-out by combining two or more sampled data points which have been acquired at different times such that the number of new data points for read-out are less than the number of sampled data points.

In this way, the amount of produced data is reduced, while still enabling accurate image reconstruction and/or mitigating aliasing.

DETAILED DESCRIPTION

Figure 1:
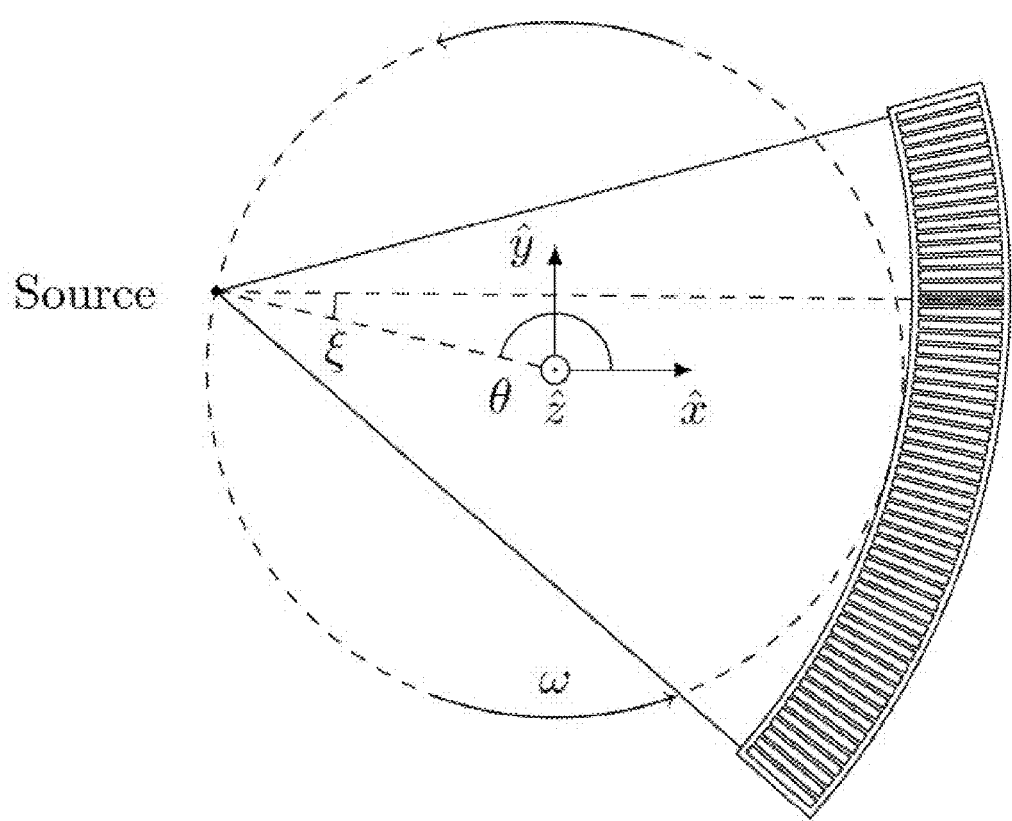
FIG. 1 is a schematic diagram illustrating an example of a CT geometry.
Figure 2:
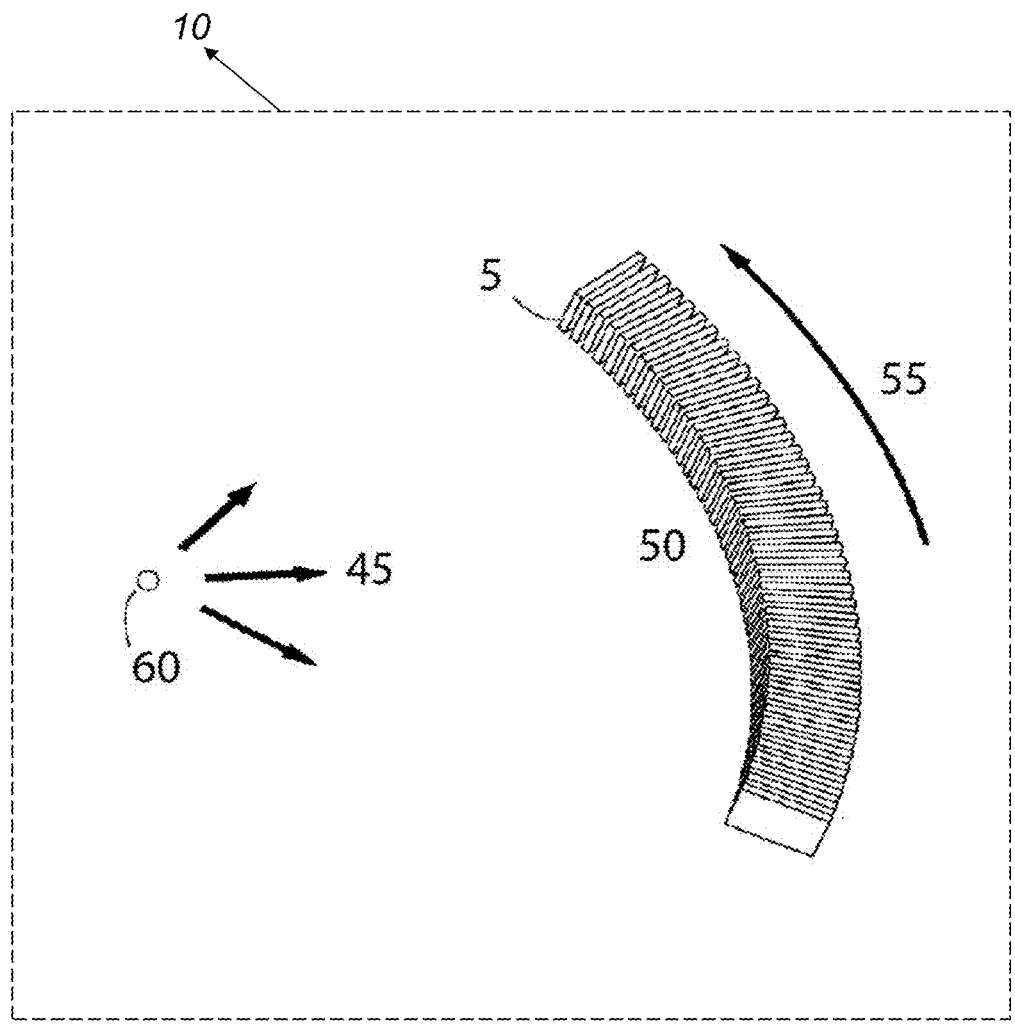
FIG. 2 is a schematic diagram illustrating an example of a CT geometry using edge-on detectors.
Figure 3:
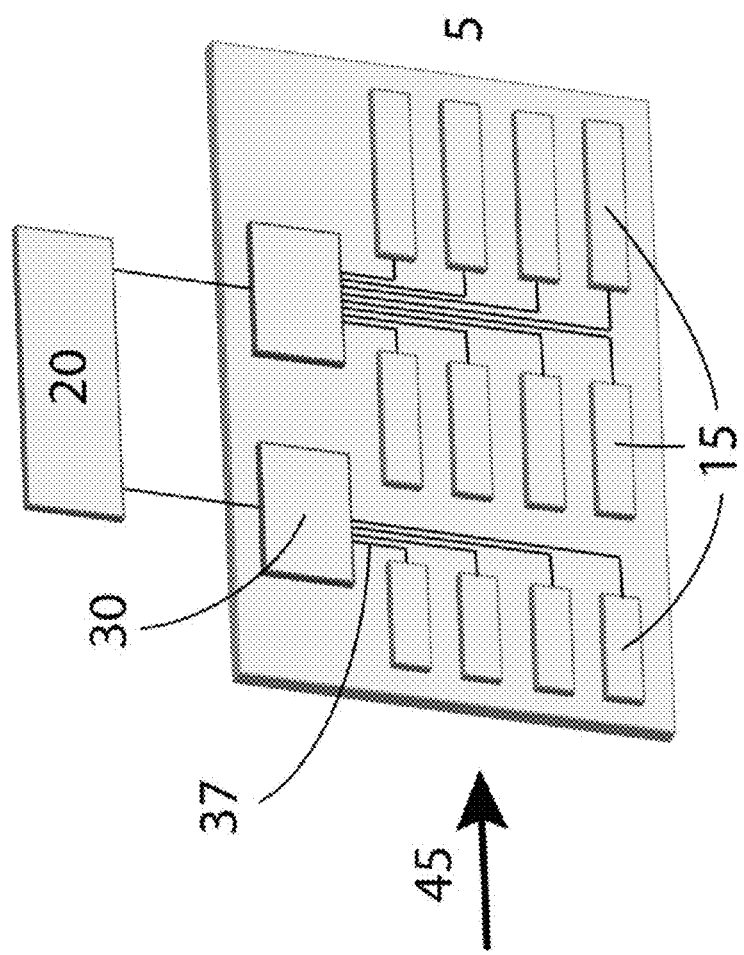
FIG. 3 is a schematic diagram illustrating an example of a semiconductor detector module implemented as a so-called multi-chip module.
Figure 4:
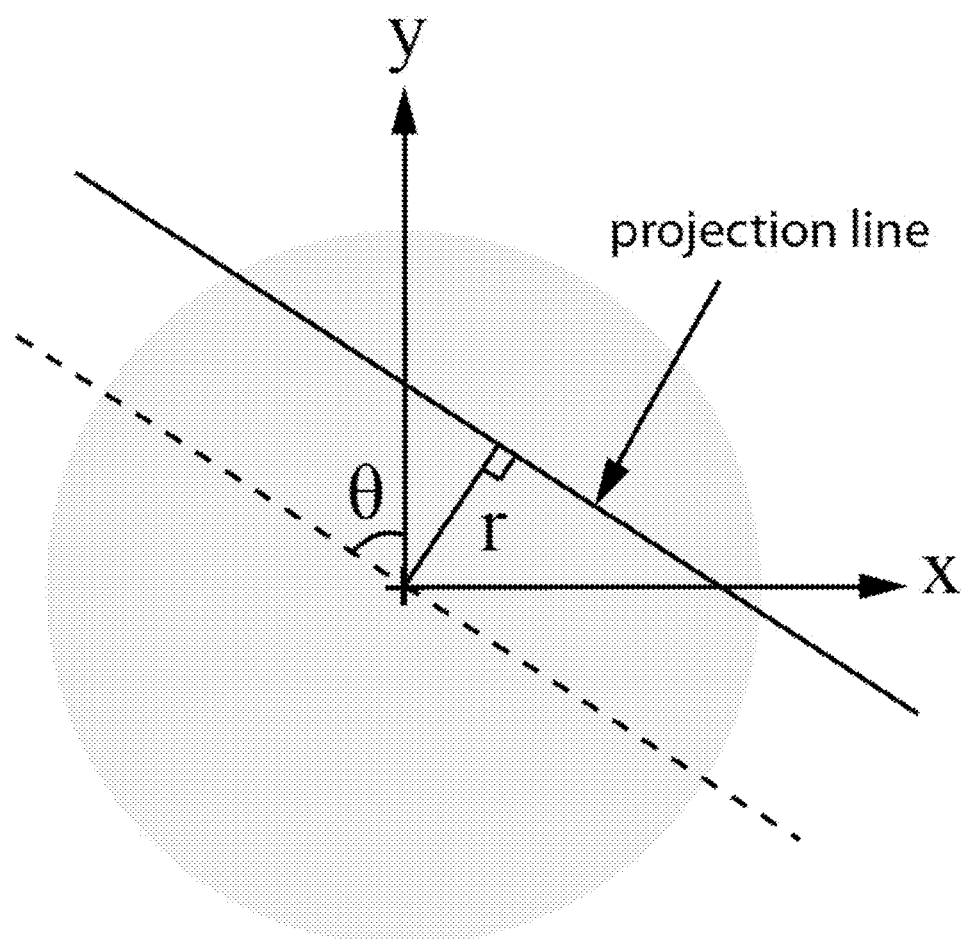
FIG. 4 is a schematic diagram illustrating an example of a projection line defined by an angular coordinate, θ, and a radial coordinate, r.
Figure 5:
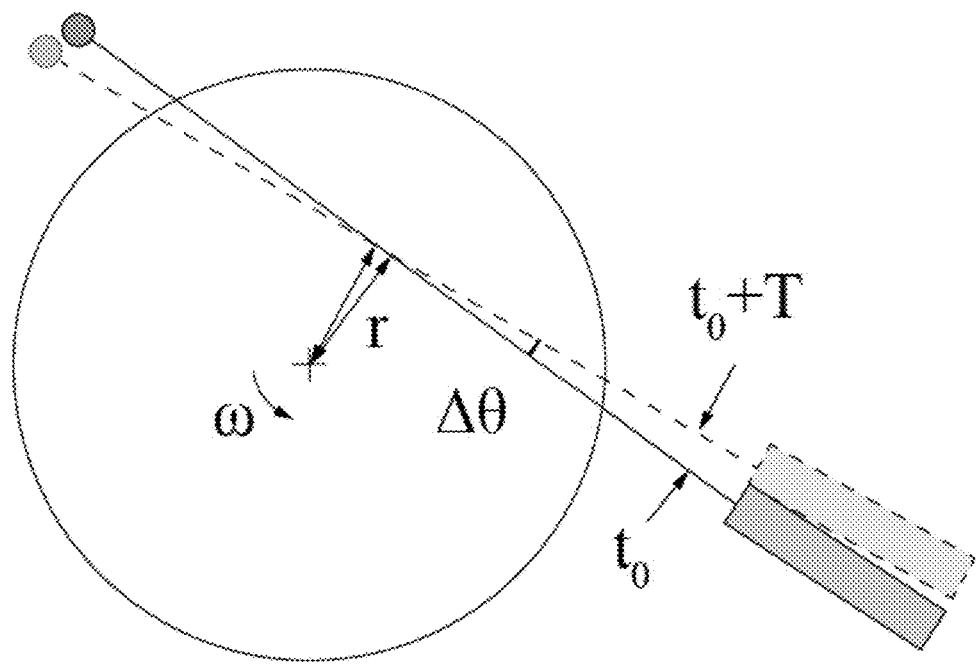
FIG. 5 is a schematic diagram illustrating an example of angular sampling.
Figure 6:
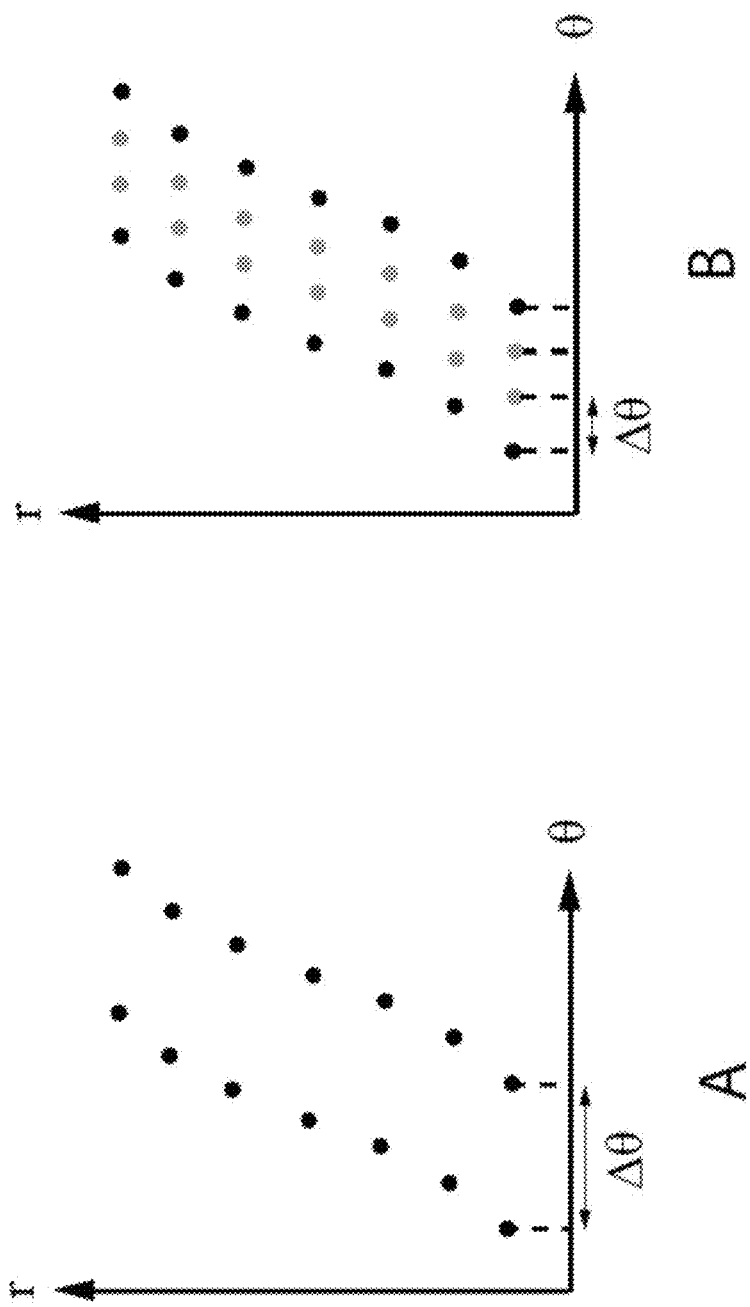
FIGS. 6A-B are schematic diagrams illustrating an example of how a detector array, similar to that displayed in FIG. 1, samples the sinogram space for two different angular positions of the gantry separated by Δθ

As mentioned, the angular sampling rate in e.g. CT is generally limited by the rate at which data can be read out from the measurement circuit of the x-ray detector. The measurement circuit of the detector can, however, have the capacity to sample at a higher rate than the data read-out chain can handle. Also, the inventors have recognized that it may be possible that the measurement circuit can perform some operations, such as addition or multiplication, during the time between samples. Here, a solution is proposed in which the data is processed in the measurement circuit before read-out. The processing may involve producing new data points by combining two or more data points which have been acquired at different times. Further, the number of data points which are read out are less than the number of original data points.

By way of example, the data points may be regarded as data samples generated by the measurement circuit when sampling measurement data.

In a first aspect, there is provided a measurement circuit for an x-ray detector, wherein the measurement circuit is configured to sample measurement data to generate data points and process the data points before read-out to produce new data points by combining two or more data points which have been acquired at different times such that the number of data points for read-out are less than the number of original data points.

By way of example, the measurement circuit is configured to process the data points by any combination of summation, linear combination or non-linear combination.

As an example, the measurement circuit is configured to process data from more than one detector element of the x-ray detector.

It should though be understood that the measurement circuit may be configured to process data from one or more detector elements in general.

In a particular example, the measurement circuit is configured to sum data from two or more detector elements before or after the signal is low-pass filtered and down-sampled.

For example, the measurement circuit comprises a processing unit configured to decimate the data signal from a higher sampling rate to a lower sampling rate for data read-out, while mitigating aliasing using a digital low-pass filter.

As an example, the processing unit comprises the digital low-pass filter followed by a down-sampling module for decimating the data signal from the higher sampling rate to the lower sampling rate for data read-out.

Normally, the measurement circuit may be configured to process electric charge generated from x-rays to obtain the measurement data.

By way of example, the measurement circuit may be configured to generate measurement data in the form of photon counts and/or estimated energy. In the latter case, the estimated energy (or equivalently charge) may be estimated photon energy and/or integrated energy.

According to a second aspect, there is provided a method for processing data by a measurement circuit of an x-ray detector prior to data read-out, wherein new data points are produced by combining two or more data points which have been acquired by the measurement circuit at different times such that the number of data points which are read out are less than the number of original data points.

By way of example, the processing includes an anti-aliasing filtration by convolution followed by a down-sampling before readout. For example, the data signal is filtered using a low-pass filter and down-sampled before for read-out.

Optionally, the measurement circuit decreases aliasing in the data signal and the low-pass filter enables down-sampling without introducing aliasing.

In a particular example, the processing includes data from several detector elements of the x-ray detector.

For example, the processing may include summing data from two or more detector elements before or after the signal is low-pass filtered and down-sampled.

Normally, the processing may include any combination of summation, linear combination or non-linear combination of the original, or new data points.

As an example, the pattern of how to combine the data points in order to create the new data points is stored on a memory in the measurement circuit.

According to a third aspect, there is also provided an x-ray imaging system comprising a measurement circuit as described herein. The x-ray imaging system comprises also comprises well-accepted detector and/or imaging technology such as a digital image processing system, which in combination with the measurement circuit described herein provides improved image reconstruction.

Figure 9:
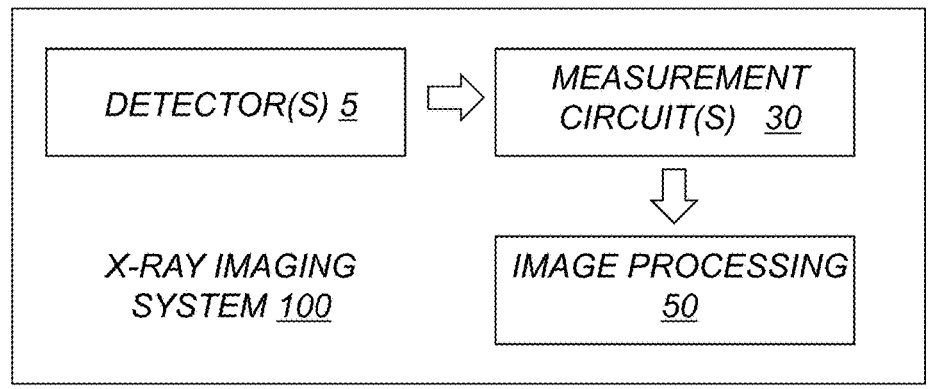
FIG. 9 is a schematic diagram illustrating an example of an x-ray imaging system.

FIG. 9 is a schematic diagram illustrating an example of an x-ray imaging system. In this example, the x-ray imaging system 100 includes one or more detectors 5, each of which may have a number of detector elements, and one or more measurement circuits 30, and an image processing module 50.

By way of example, the x-ray imaging system may be a Computed Tomography (CT) system.

According to a fourth aspect, there is provided a measurement circuit for an x-ray detector having a number of detector elements. The measurement circuit is configured for connection to the detector elements of the x-ray detector to obtain measurement data. The measurement circuit is configured to sample the measurement data to generate data samples, also referred to as sampled data points. The measurement circuit is further configured to process the sampled data points before read-out to produce new data points for read-out by combining two or more sampled data points which have been acquired at different times such that the number of new data points for read-out are less than the number of sampled data points.

In a particular example, the proposed technology relates to oversampling and anti-aliasing filtration in measurement circuit such as an ASIC sequencer for an x-ray detector in e.g. Computed Tomography.

Expressed slightly differently, the proposed technology relates to a measurement method performed, e.g. by a Computed Tomography system. The proposed technology also relates to devices and systems configured to perform the measurement method.

In other words, there is provided a measurement method in which the data is processed by the measurement circuit of the detector prior to the data read-out. The proposed processing comprises a step in which new data points are produced by combining two or more data points which have been acquired at different times. Further, the number of data points which are read out are less than the number of original data points.

In an example embodiment, the processing includes an anti-aliasing (low-pass) filtration by convolution followed by a downsampling before readout.

This method reduces the amount of produced data while mitigating aliasing.

In a particular example, the proposed technology involves the application of digital decimation of the signal in the measurement circuit of an x-ray detector used e.g. in CT. A benefit is that the proposed technology prevents aliasing artifacts in the angular (temporal) signal, e.g. in CT.

In an example embodiment, the signal is filtered using a low-pass filter and downsampled to match the requirements of the output rate. The higher internal sampling rate of the measurement circuit decreases the aliasing in the signal and the low-pass filter then enables downsampling without introducing aliasing; a process referred to as decimation.

In an alternative embodiment, the processing includes data from several detector elements. For example, the processing can include summing the data from two or more detector elements before or after the signal is low-pass filtered and downsampled.

In an example embodiment, the pattern of how to combine the data points in order to create the new ones is stored on a memory in the measurement circuit. For example, if a so-called tent convolution kernel is employed as a low-pass filter, the data new data points are formed by a linear combination of three original data points with coefficients e.g. ¼, ½, ¼. The pattern may include any combination of summation, linear combination or non-linear combination of the original, or new data points. For example, the pattern can include forming new points using linear combination similar to the tent kernel described above followed by, for example, a summation of the new points formed using the tent kernel.

Figure 7:
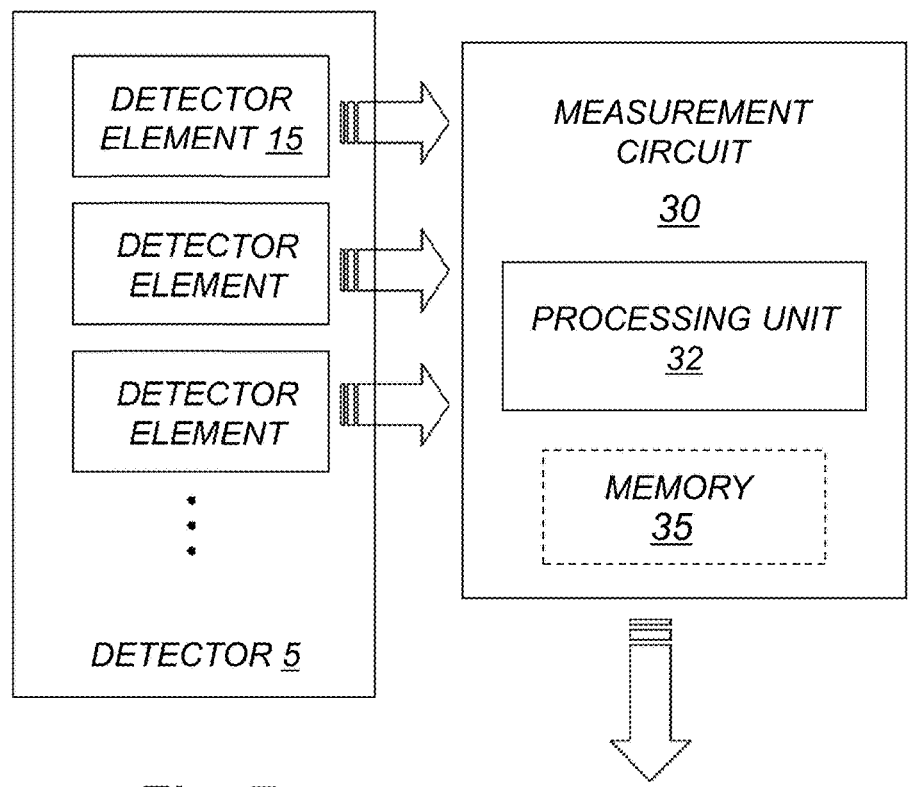
FIG. 7 is a schematic diagram illustrating an example of a measurement circuit for an x-ray detector.

FIG. 7 displays a schematic illustration of an example of a measurement setup of a detector where the measurement circuit 30 comprises a processing unit 32. Each detector element 15 of a detector may be connected individually to the measurement circuit 30. The measurement circuit 30 processes the electric charge generated from each x-ray and converts it to digital data, which can be used to obtain measurement data such as a photon count. The detector may be a photon-counting (edge-on) detector. It should though be understood that the invention is not limited thereto, and that the detector may also be a charge/energy-integrating detector. In a particular example, the measurement circuit 30 may comprise one or many counters (shown in FIG. 8), which count the number of x-rays detected by a detector element 15 within a measurement period. The measurement circuit may in particular embodiments comprise a memory 35 used for storing data during the data sampling and/or data processing.

The measurement circuit 30 may also comprise one or several processors or processing circuitries, hereinafter referred to as a processing unit 32. Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs), or Application Specific Integrated Circuitry (ASIC).

Figure 8:
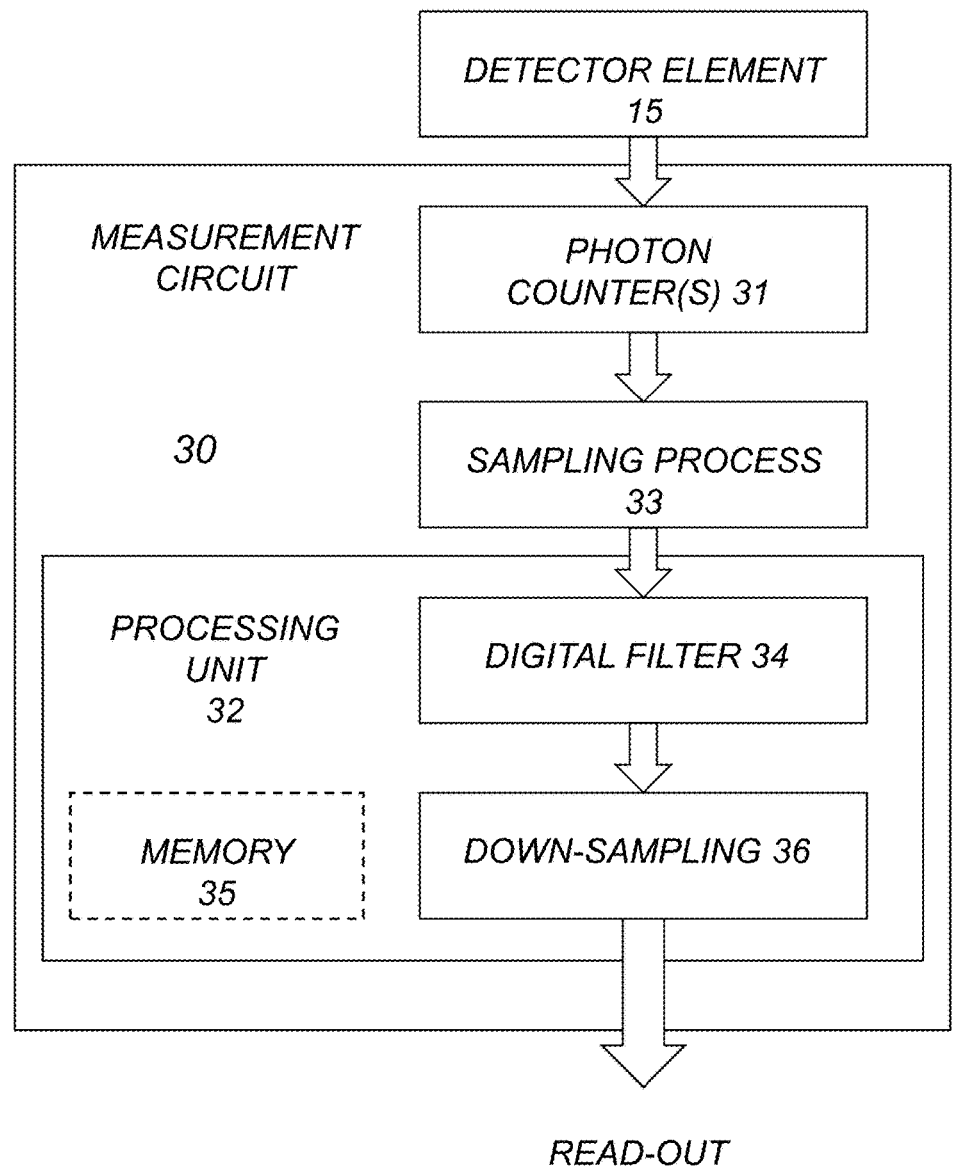
FIG. 8 is a schematic diagram illustrating a more detailed example of a measurement circuit for an x-ray detector.

In the example embodiment illustrated in FIG. 8, the measurement circuit 30 comprises one or more counters 31, a corresponding sampling module 33 for performing a sampling process, and a processing unit 32. The processing unit 32 may comprise, according to an example embodiment, a digital filter 34 followed by a down-sampling module 36.

In this particular example, the processing unit 32 may include the memory 35.

In a particular example, the processing unit 32 is configured to decimate the signal from a higher sampling rate in the measurement circuit to a lower sampling rate for data read-out, while mitigating aliasing in the signal using a low-pass digital filter, as previously described.

The steps, functions, procedures, and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, and/or blocks described herein may be implemented in software such as a computer program for execution by suitable processing circuitry such as one or more processors or processing units.

It should also be understood that it may be possible to re-use the general processing capabilities of any conventional device or unit in which the proposed technology is implemented. It may also be possible to re-use existing software, e.g. by reprogramming of the existing software or by adding new software components.

It will be appreciated that the methods and arrangements described herein can be implemented, combined and re-arranged in a variety of ways.

For example, embodiments may be implemented in hardware, or in software for execution by suitable processing circuitry, or a combination thereof.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

The invention claimed is:

1. A measurement circuit for an x-ray detector, wherein the measurement circuit is configured to sample measurement data to generate data points and process the data points before read-out to produce new data points by combining two or more data points which have been acquired at different times such that the number of data points for read-out are less than the number of original data points, wherein the measurement circuit is configured to process data from more than one detector element of the x-ray detector, and wherein the measurement circuit is configured to sum data from two or more detector elements before or after the signal is low-pass filtered and down-sampled.

2. The measurement circuit of claim 1, wherein the measurement circuit is configured to process electric charge generated from x-rays to obtain the measurement data.

3. The measurement circuit of claim 2, wherein the measurement circuit is configured to generate measurement data in the form of photon counts and/or estimated energy.

4. A measurement circuit for an x-ray detector, wherein the measurement circuit is configured to sample measurement data to generate data points and process the data points before read-out to produce new data points by combining two or more data points which have been acquired at different times such that the number of data points for read-out are less than the number of original data points, and wherein the measurement circuit comprises a processing unit configured to decimate the data signal from a higher sampling rate to a lower sampling rate for data read-out, while mitigating aliasing using a digital low-pass filter.

5. The measurement circuit of claim 4, wherein the processing unit comprises the digital low-pass filter followed by a down-sampling module for decimating the data signal from the higher sampling rate to the lower sampling rate for data read-out.

6. An x-ray imaging system comprising a measurement circuit of claim 4.

7. The x-ray imaging system of claim 6, wherein the x-ray imaging system is a Computed Tomography (CT) system.

8. The measurement circuit of claim 4, wherein the measurement circuit is configured to process data from more than one detector element of the x-ray detector.

9. The measurement circuit of claim 4, wherein the measurement circuit is configured to process the data points by any combination of summation, linear combination or non-linear combination.

10. The measurement circuit of claim 4, wherein the measurement circuit is configured to process electric charge generated from x-rays to obtain the measurement data.

11. The measurement circuit of claim 10, wherein the measurement circuit is configured to generate measurement data in the form of photon counts and/or estimated energy.

12. A method for processing data by a measurement circuit of an x-ray detector prior to data read-out, wherein new data points are produced by combining two or more data points which have been acquired by the measurement circuit at different times such that the number of data points which are read out are less than the number of original data points, and wherein the processing includes an anti-aliasing filtration by convolution followed by a down-sampling before readout.

13. The method of claim 12, wherein the processing includes data from several detector elements of the x-ray detector.

14. The method of claim 12, wherein the processing includes any combination of summation, linear combination or non-linear combination of the original, or new data points.

15. The method of claim 12, wherein the pattern of how to combine the data points in order to create the new data points is stored on a memory in the measurement circuit.

16. A method for processing data by a measurement circuit of an x-ray detector prior to data read-out, wherein new data points are produced by combining two or more data points which have been acquired by the measurement circuit at different times such that the number of data points which are read out are less than the number of original data points, and wherein the data signal is filtered using a low-pass filter and down-sampled before for read-out.

17. The method of claim 16, wherein the measurement circuit decreases aliasing in the data signal and the low-pass filter enables down-sampling without introducing aliasing.

18. A method for processing data by a measurement circuit of an x-ray detector prior to data read-out, wherein new data points are produced by combining two or more data points which have been acquired by the measurement circuit at different times such that the number of data points which are read out are less than the number of original data points, wherein the processing includes data from several detector elements of the x-ray detector, and wherein the processing includes summing data from two or more detector elements before or after the signal is low-pass filtered and down-sampled.

* * * * *